United States Patent [19]

Darkwa et al.

[11] Patent Number: 5,293,885
[45] Date of Patent: Mar. 15, 1994

[54] HAIR RELAXER AND POST-RELAXER HAIR BRIGHTENER SYSTEM

[75] Inventors: Adu G. Darkwa, Chicago; Apolonio Villanueva, III, Northbrook, both of Ill.

[73] Assignee: Johnson Products Co., Inc., Chicago, Ill.

[21] Appl. No.: 728,572

[22] Filed: Jul. 11, 1991

[51] Int. Cl.$^5$ ............ A61K 7/06; A61K 7/08
[52] U.S. Cl. ............ 132/209; 132/203; 132/204; 132/208; 424/70; 424/71
[58] Field of Search ........... 132/203, 204, 205, 208, 132/209; 424/70, 71

[56] References Cited

U.S. PATENT DOCUMENTS

| | | | |
|---|---|---|---|
| 3,912,808 | 10/1975 | Sokol | 424/71 |
| 4,027,008 | 5/1977 | Sokol | 424/62 |
| 4,175,572 | 11/1979 | Hsiung et al. | 132/204 |
| 4,303,085 | 12/1981 | de la Guardia et al. | 132/203 |
| 4,304,244 | 12/1981 | de la Guardia | 132/204 |
| 4,314,572 | 2/1982 | de la Guardia et al. | 132/204 |
| 4,324,263 | 4/1982 | de la Guardia | 132/204 |
| 4,327,751 | 5/1982 | Evans | 132/208 |
| 4,373,540 | 2/1983 | de la Guardia | 132/204 |
| 4,381,920 | 5/1983 | Garlen | 8/406 |
| 4,416,296 | 11/1983 | Meyers | 132/203 |
| 4,602,648 | 7/1986 | Syed et al. | 132/204 |
| 4,772,462 | 9/1988 | Boothe et al. | 424/70 |
| 4,898,726 | 2/1990 | Den Beste | 424/72 |
| 4,992,267 | 2/1991 | Den Beste et al. | 424/71 |

FOREIGN PATENT DOCUMENTS 8902233  3/1989  PCT Int'l Appl.

OTHER PUBLICATIONS

Starch, M., "Silicone for Conditioning Damaged Hair," *Soap/Cosmet./Chem. Specialties*, pp. 34–39 (Apr., 1986).
"Merquat© 280," Bulletin 30–106C, Calgon Corporation (undated).
"Dow Corning© Q2-7224 Conditioning Agent", Technical Bulletin Form No. 22-956-83, Dow Corning Corporation (1983).

Primary Examiner—Gene Mancene
Assistant Examiner—Frank A. LaViola
Attorney, Agent, or Firm—Olson & Hierl, Ltd.

[57] ABSTRACT

A hair relaxer and post-relaxer hair brightener system and method is disclosed which overcomes the undesirable alteration of the natural tone of hair, especially of naturally gray hair, by highly-alkaline hair-relaxing systems. The natural tone of such alkali-relaxed hair is desirably brightened, enhanced and restored in a hair brightening step by certain disclosed post-relaxer aqueous hair brightener compositions which contain an active hair brightening agent. In a particularly preferred embodiment, the hair brightening agent comprises a relatively low active concentration of hydrogen peroxide.

42 Claims, No Drawings

HAIR RELAXER AND POST-RELAXER HAIR BRIGHTENER SYSTEM

TECHNICAL FIELD

This invention relates to the straightening or relaxing of naturally curly hair with highly-alkaline hair relaxer systems and to post-relaxer aqueous hair brightener compositions and methods for improving the natural tone of the relaxed hair.

BACKGROUND ART

Highly-alkaline hair-relaxing or hair-straightening compositions are well known in the art and are commonly used in salons and in the home. These compositions usually have a highly-alkaline pH of above about 12 to about 14 due to the presence of an effective hair-relaxing or hair-straightening amount of water-soluble strongly alkaline material. Because of their causticity, highly-alkaline compositions, in some instances, alter the natural tone of human hair undesirably as discussed below. There is a desire and long-standing need to overcome this disadvantage during or before completing the hair-relaxing or hair-straightening process.

For convenience, the terms "hair-relaxing," "hair-texturizing," "hair-straightening" and grammatical variations thereof are used interchangeably herein to denote the chemical loosening or removal of some or substantially all of the naturally tight curl pattern from naturally curly or wavy hair at a pH above about 12. Generally, the term "permanent hair-straightening" denotes the removal of substantially all curliness to achieve a visibly straight configuration, whereas the terms "hair-relaxing" and "texturizing hair-straightening" each denotes varying degrees of loosened wave patterns. Most modern commercial products are commonly called hair relaxers, so this term will be used hereafter to encompass all of the foregoing products for ease and simplicity and not by way of limitation.

The term "tone" as used herein includes the natural color of the hair and those visually desirable characteristics normally associated therewith, such as highlights, brightness and shine or luster. For example, at high alkalinity the natural tone of dark brown hair is reddened, and the naturally "white" fibers of gray hair are undesirably and visibly yellowed and their normal highlighting brightness is correspondingly visibly dulled. Thus, the natural shine or luster of such alkali-treated hair, especially gray hair, is delustered and drabbed of its desirable highlights. The term "gray hair" denotes "head hair" which, en masse, is visibly subjectively classifiable as containing from about 1 percent to about 100 percent naturally "white" fibers; i.e., unpigmented. Thus, the term "gray hair," as used herein, encompasses albino hair, as well as hair commonly described as "salt and pepper" which has lost some or all of its natural pigmentation through normal aging.

Depending on the coarseness, degree of curliness, and resistance of the hair being relaxed, the user typically selects either a mild-strength, regular-strength or super-strength relaxer composition and varies the timing of the relaxing procedure by leaving the hair-relaxing composition in contact with the hair only long enough to remove the desired amount of curl. Consequently, the altered natural tone of alkali-relaxed hair becomes more noticeable and objectionable either as the alkaline strength of the composition increases, as the length of time increases in which the hair is in contact with the highly-alkaline relaxer composition, or when both conditions occur.

Naturally gray hair, in particular, when it is relaxed at high-alkalinity, develops, in some cases, an undesirable noticeable greenish yellow to yellowish brown tinge. This post-relaxer effect is commonly called "yellowing" or "discoloration." For convenience, the term "yellowing" and its grammatical variations will be used hereafter to denote any visibly altered tone of natural gray hair generally associated with the undesirable unnatural yellowish tinge caused by alkali-type hair relaxing. This type of yellowing is distinct from alterations in the tone of hair caused by environmental pollution, smoking, sun fading, and the like.

The mechanism of why the natural tone of the hair is altered by highly-alkaline hair-relaxing compositions is not understood but is generally attributed to the action of certain strong bases normally required for effective alkali-type hair-relaxing. The term "alkali-type hair-relaxing" as used herein refers to chemically relaxing hair at a highly-alkaline pH of above about 12, in which the sole hair-relaxing agent is a water-soluble strong chemical base. Naturally curly hair which has been subjected to alkali-type hair relaxing is generally referred to herein as "alkali-relaxed" hair. The term "naturally curly hair" denotes virgin hair having a tight curl or wave pattern and will be referred to herein generally as "hair", for convenience. At high alkalinity, strong chemical bases are known to convert the disulfide bonds of cystine in hair to stable, irreversible crosslinks of primarily lanthionine and some lysinoalanine. Thus, unlike thiol or bisulfite relaxers, a chemical oxidative or alkaline re-linking step is unnecessary.

Hence, the only step required following an alkali-type relaxing process is to promptly remove the hair relaxing composition by rinsing the hair with water, and substantially neutralize all excess alkaline material remaining to avoid and minimize damage to the hair protein or skin. For this purpose, a non-alkaline base-neutralizing shampoo is commonly used to neutralize and remove excess residual alkaline material from the hair and scalp. The terms "neutralizer" and "neutralizer shampoo," therefore, are used herein to generally denote a post-relaxer composition capable of accomplishing the foregoing neutralization of residual alkalinity when it is applied substantially immediately following the removal of hair-relaxing composition from the hair.

The term "strong base" as used herein denotes cosmetically useful water-soluble, non-volatile inorganic caustic bases and relatively strong organic bases capable of relaxing the hair. For example, alkali metal hydroxide, such as sodium hydroxide (lye), potassium hydroxide, or lithium hydroxide; alkali earth metal hydroxide, such as calcium hydroxide, barium hydroxide and strontium hydroxide or oxides thereof capable of forming hydroxides in water; or a relatively strong organic base, such as guanidine, guanidine hydroxide or quaternary ammonium hydroxide is usually used.

Modern highly-alkaline hair relaxers are commonly called "no-base" hair relaxers and are referred to as "lye," "non-lye" and "no-lye" hair relaxers as discussed below. The term "no-base" in referring to hair relaxers means that the scalp need not be coated with a skin-protective oleaginous base, such as petrolatum, mineral oil and lanolin, before applying a highly-alkaline hair relaxer. The term "no-base hair relaxer," therefore, as used herein generally encompasses a highly-alkaline hair-relaxing product in which some of the skin protective oleaginous material is emulsified in an aqueous composition, preferably in the form of a viscous cream, and does not require the use of a skin-protective base. No-base hair relaxers are commercially supplied as either a "single product" kit or a "two-part product" kit.

In commercial practice, a single product relaxer kit generally denotes a no-base hair relaxer formulation which usually contains, as the sole active hair-relaxing agent, an alkali metal hydroxide. When the alkali metal hydroxide is a caustic base such as sodium hydroxide or potassium hydroxide, the composition is generally referred to as a "lye-type" hair relaxer. When the active hair-relaxing agent is lithium hydroxide or a salt of a strong base, such as sodium carbonate, the composition is referred to herein as a "non-lye" hair relaxer. The product is generally applied in the form of a viscous emulsion cream directly from its container to the hair for use.

A particularly popular type of no-base formulation is commonly called a "no-lye" hair relaxer. The term "no-lye" means that the active hair-relaxing agent is an organic chemical base instead of inorganic caustic base (lye). In commercial practice, the relatively strong organic chemical base, guanidine is usually present in the form of guanidine hydroxide in a no-lye hair relaxer. Guanidine hydroxide, however, is not generally stable for long periods in aqueous solutions, so it must be prepared fresh just before using.

Consequently, no-base, no-lye type hair relaxers are usually supplied commercially as a two-part product relaxer kit in which the guanidine hydroxide is generally prepared in situ from guanidine carbonate and calcium hydroxide. Hence, one part of the product contains the guanidine carbonate packaged in substantially liquid aqueous form, commonly called the "activator." The other part of the product is a package containing relatively high amounts of about 4 percent to about 7 percent calcium hydroxide emulsified in the form of a viscous cream. Prior to using, the consumer or beautician mixes the cream and activator portions of the kit together. The resulting no-base, no-lye hair relaxer cream is then applied to the hair relatively promptly (preferably within several hours and less than 24 hours). For convenience, the term no-lye hair relaxer, therefore, refers to the foregoing admixture.

The yellowing of the tone of naturally gray relaxed hair is more pronounced after a no-base, no-lye hair relaxer is used than when a lye-type hair relaxer is used. A yellow tinge on gray hair is particularly undesirable, because the white fibers in gray hair normally have a desirable natural bright tone which gives the hair highlights, whereas when yellowed, the hair looks dull, drab and lackluster.

Even though some or most of the visible yellowing caused by alkali-type hair relaxing sometimes gradually fades over a period of days, most persons generally find this yellowing highly objectionable. Consequently, the majority of consumers resort to some remedial masking of any persistent post-relaxer yellowish tinge by applying a temporary or semipermanent hair coloring, usually a violet or silver rinse. However, such colorant rinses can produce further unnatural or unsatisfactory tones, such as greens and blues.

Some success in removing visible yellowish tinges which persist in the interim between relaxer treatments has been achieved with an oily color corrective product known in the professional salon arts when it is mixed with a relatively high concentration of hydrogen peroxide of above about 5 percent. However, this practice is unsatisfactory, because at concentrations above about 3 percent, hydrogen peroxide can irritate or burn the scalp or skin, bleach the natural underlying color of the hair and increase the risk of chemical damage to the virgin outgrowth portion of the hair on later receiving a hair relaxer treatment.

Some strides have been made in formulating lye-type hair relaxer compositions that are substantially non-yellowing to gray hair during the hair relaxing step by including hair keratin-disulfide reducing agents having functional sulfhydydrol groups, such as dimercaptoadipic acid or cysteine, as ingredients of the alkaline relaxer cream. See U.S. Pat. Nos. 4,898,726 and 4,992,267, respectively, which issued to the present assignee and the disclosures of which are incorporated herein by reference. However, the vast majority of popular hair relaxers otherwise formulated and presently sold do not contain the foregoing beneficial ingredients.

Therefore, the need to overcome tonal alteration problems before the alkali relaxing process is completed when conventional no-base hair relaxer systems are used still exists, particularly during the use of no-base, no-lye hair relaxer systems.

An ideal solution is to provide a relatively simple hair relaxer system and method for enhancing and restoring a natural tone to alkali-relaxed hair, especially to alkali-relaxed gray hair, in a post-relaxing step performed prior to completing a hair relaxing treatment. The hair relaxer and post-relaxer hair brightener system and method of this invention provides such a solution to this long-standing need.

SUMMARY OF THE INVENTION

This invention relates to a hair relaxer and post-relaxer hair brightener system and method which overcomes problems of undesirable alteration of the natural tone of hair, especially naturally gray hair, resulting during alkali-type hair relaxing. This benefit is obtained as part of the hair-relaxing treatment by practicing a post-relaxer hair brightening step substantially immediately following the removal of alkaline hair relaxer and neutralization of residual alkalinity in the alkali-relaxed hair, as disclosed and described herein.

Thus, a post-relaxer hair brightener composition embodying the principles of this invention comprises an effective amount of active hair brightening agent when it is applied in the foregoing step to neutral, alkali-relaxed hair in need of tonal brightening. In practicing the hair brightening step, a practical total contact period of less than about 15 minutes is sufficient, and the hair brightener composition is preferably removed by rinsing the brightened hair with water. Most preferably, visible hair brightening is achieved substantially immediately on contact with hair brightener composition to within a total contact period of about 5 minutes.

The term "hair brightening" and its grammatical variation "hair brightener" is used herein to denote visible enhancement to and restoration of the natural tone of alkali-relaxed hair whose tone was undesirably altered by alkali-type relaxing as discussed earlier. The term "active hair brightening agent" denotes a material capable of brightening the tone of alkali-relaxed hair in a post-relaxing hair brightening step practiced as described above, when it is applied from an aqueous composition having a physiologically acceptable pH and is present in sufficient effective amount to visibly brighten the hair without sacrificing the hair relaxing benefits and without bleaching or imparting added color to the natural color of the hair.

Surprisingly, yellowed alkali-relaxed hair was desirably brightened with a post-relaxer hair brightener composition comprising, as the active hair brightening agent, hydrogen peroxide, present at a relatively low concentration obtained from a material which is a source or donor of hydrogen peroxide in water, such as a water-soluble per-compound which releases hydrogen peroxide in water and hydrogen peroxide.

This finding was particularly surprising because hydrogen peroxide is not normally applied to alkali-relaxed hair in any step of a conventional alkali hair-relaxing process and, moreover, would generally be avoided. Hydrogen peroxide is, of course, generally associated with thiol permanent waving systems in which thiol hair reducing agents are used since the broken disulfide bonds in the thiol-reduced hair must be oxidatively re-linked, typically by applying compositions called neutralizers containing hydrogen peroxide, perborate salt, bromate salt and like oxidants. In contrast, as discussed earlier, alkali-type relaxing does not require any post-relaxing chemical relinking step. All that is required is to remove and substantially neutralize all excess alkaline material.

Another surprising finding was that yellowed alkali-relaxed hair was brightened when the active hair brightening agent was a cosmetically acceptable water-soluble aliphatic organic acid having hydroxyl or mercapto substituent groups and less than about 7 carbon atoms per molecule and salts thereof applied from an aqueous composition as described above.

One preferred hair relaxer and post-relaxer hair brightener system aspect of this invention comprises at least three individual components, each intended for use in a separate and sequential step of an alkali-type hair-relaxing process. Component (i) comprises a no-base highly-alkaline hair relaxer composition, preferably in the form of a viscous cream, having a pH of above about 12 and containing an effective hair-relaxing amount of strong base. Component (ii) comprises an aqueous, non-alkaline, base-neutralizing composition, preferably in the form of a shampoo and component (iii) comprises an aqueous post-relaxer hair brightener composition comprising an effective amount of active hair brightening agent.

A particularly preferred hair brightening composition comprises about 1 weight percent to about 2 weight percent hydrogen peroxide equivalent in water and sufficient acidifying agent or alkalizing agent to provide a physiologically acceptable pH.

One preferred method aspect of this invention comprises the steps of sequentially first applying to naturally curly hair a hair relaxer composition generally according to component (i) of the foregoing system, by methods well known in the art to at least partially relax or straighten those portions of the hair that have received no prior chemical hair relaxing treatment, i.e., substantially virgin outgrowth. It is generally well known that the length of time that the hair is exposed to a highly alkaline relaxer varies with the amount of curl in the hair and the strength of the alkaline straightening agent. Typically, this length of time is determined by the practitioner based on the amount of partial or complete removal of natural curl desired. Less than about 20 minutes, preferably less than about 15 minutes to about 18 minutes, is desirable.

Thereafter, substantially all of the hair relaxer composition contacting the alkali-relaxed hair is then removed by rinsing the relaxed hair with water and a non-alkaline base-neutralizing composition according to component (ii) of the foregoing system is then applied to the rinsed hair while it is still substantially wet. This base-neutralizing composition preferably has a pH of less than about 8 to substantially neutralize and complete the removal of residual alkalinity from the relaxed hair in one or more applications. Each application is removed by rinsing the alkali-relaxed hair at least once with water to leave the wet alkali-relaxed hair substantially neutral.

While the neutral, alkali-relaxed hair is still substantially wet, an aqueous hair brightener composition according to component (iii) is applied to those portions of the alkali-relaxed hair that have been visibly altered in tone and distributed therethrough. The hair is so contacted for a sufficient practical hair brightening period of about 0.5 minutes to less than about 15 minutes. Thereafter, the hair brightener composition is removed from the brightened hair by rinsing it with water.

In another preferred hair relaxer and hair brightener system aspect of this invention, the alkali-relaxed hair is simultaneously brightened and conditioned. For this purpose, at least one hair conditioning agent is included in a hair brightener composition generally according to component (iii) of the above system. Alternatively, another conditioning system aspect of the above system can further include a separate hair conditioning component (iv) separately packaged and intended for use in a separate hair conditioning step of a hair relaxer and post-relaxer hair brightener method aspect of this invention. Component (iv) preferably comprises a composition having a pH of less than about 8, more preferably of less than about 7, containing an effective hair-conditioning amount of a cationic compound, In one method aspect, the method described above can further include a hair-conditioning step comprising applying a composition generally according to component (iv) to the hair either in a pre-relaxing step before applying component (i), or in a pre-neutralizing step between the removal of component (i) and the application of component (ii) or in both of each of the foregoing steps, with or without a water rinse step subsequent to each application.

One major surprising benefit is that the objectionable yellowish tinge produced on alkali-relaxed naturally gray hair, particularly by no-base, no-lye hair relaxer systems in which guanidine hydroxide is the active hair-relaxing agent, is overcome substantially immediately on contact to within less than about 10 minutes total contact with a post-relaxer hair brightener composition containing relatively low concentrations of hydrogen peroxide as practiced in the system and method of this invention.

In addition, the tone of alkali-relaxed yellowed gray hair can be desirably brightened by a hair relaxer and hair brightener system of this invention without sacrificing the beneficial effectiveness of the hair relaxer and at the same time gaining the benefit of improved tonal appearance before completing the hair-relaxing process. Thus, there is no need for the customer to resort to using further post-relaxer remedial colorants in the interim between relaxer treatments.

Another benefit is that the natural tone of alkali-relaxed hair is readily and easily enhanced or restored by a post-relaxer hair brightener composition of this invention when it is used as a component of a system and method as disclosed herein. A further benefit is that relaxed hair can be simultaneously conditioned and brightened with a conditioning hair brightener composition by practicing the principles of this invention.

Still further advantages and benefits will be apparent to those skilled in the art from the description, examples and claims which follow.

DETAILED DESCRIPTION OF THE INVENTION

It has now been found that alterations in the natural tone of hair, and gray hair in particular, resulting from alkali-type relaxing can be readily overcome within a practical time period in conjunction with and before completing a hair relaxer process. This problem is solved by applying a hair brightener composition comprising an effective amount of hair brightening agent to substantially neutral alkali-relaxed hair in a post-relaxing step of the hair-relaxing process.

The term "substantially neutral hair" herein denotes hair which has been exposed to a highly-alkaline hair relaxer at a pH above 12 and then subsequently exposed to a base-neutralizing environment to remove and substantially neutralize residual alkalinity on the hair. Thus the measurable pH of aqueous medium surrounding the surface of hair so treated is substantially non-alkaline, i.e., neutral to slightly acidic.

Highly-alkaline hair relaxers generally have a pH above about 12, typically from about 12.5 to about 13.8. This pH is achieved in strongly alkaline hair relaxer compositions by the presence of a sufficient hair-relaxing amount of water-soluble strong base for practicing alkali-type hair relaxing, as discussed earlier.

It is to be understood that all references hereafter to hair brightening and to hair brightener compositions refer to practicing hair brightening embodying the principles of the invention in a post-relaxing step of an alkali-type hair relaxing process as described below. It is recognized that hair brightener compositions disclosed herein can also be used, if necessary, to brighten alkali-relaxed hair which was previously yellowed from practicing conventional alkali hair relaxing methods. However, this practice is less preferred, especially if any substantial amount of virgin outgrowth is present.

As stated earlier, the term "gray hair," as used herein, denotes human head hair which encompasses naturally unpigmented "white hair", such as albino hair, as well as "salt and pepper" hair which has lost some or all of its natural pigment through normal aging. For convenience, the term "gray hair" denotes a mass of head hair where about 1 percent to about 100 percent of the total fibers are visually subjectively judged to be unpigmented. This type of criteria is commonly used by professional beauticians.

Gray hair is especially prone to yellowing by alkali-type hair-relaxing and, therefore, is benefited the most by a hair brightener composition encompassing the principles of the hair relaxer and post-relaxer hair brightener system and method of this invention. For purposes of discussing hair brightening and hair brighteners encompassing the principles of this invention, therefore, reference will be made to yellowed relaxed gray hair for illustration and not by way of limitation.

It is to be understood that, except for the post-relaxer hair brightener composition and post-relaxer hair brightening step disclosed, alkali-relaxing is otherwise practiced using generally conventional alkali hair relaxer systems and techniques. In conventional no-base lye hair relaxer systems, highly-alkaline hair relaxer cream is supplied as a single product, typically containing about 1 weight percent to about 2.5 weight percent sodium hydroxide, whereas in conventional no-base, no-lye hair relaxer systems, the hair relaxer cream is prepared from a two-part product just prior to use supplied as a liquid activator portion and an alkaline cream portion each separately packaged to be mixed together just before use to form guanidine hydroxide in situ. These hair relaxer creams are applied to hair as is commonly practiced in the hair relaxing arts and as described in more detail below.

Additionally, in conventional practice, the removal and neutralization of highly-alkaline hair relaxer from the hair is typically achieved by thoroughly rinsing the alkali-relaxed hair with tap water and then immediately shampooing the rinsed hair with a non-alkaline base-neutralizing shampoo preferably containing an acid-base indicator, such as phenolsulfonphthalein. Such an acid-base indicator assists the user in obtaining substantially neutral relaxed hair because the color of the shampoo lather visibly changes from pink at alkaline pH to white at non-alkaline pH. A particularly preferred base-neutralizing shampoo is sold for that purpose by the assignee of the invention under the trademark COLOR ALERT®.

For convenience, the present system and method of this invention is illustrated by referring to the use of a base-neutralizing shampoo but is not intended to be limited thereto. It is to be understood that any composition having pH capable of providing substantially neutral alkali-relaxed hair care can be used. For example, a hair conditioning composition which is applied to alkali-relaxed hair in a step before subsequently shampooing the alkali-relaxed hair would come within the scope of a base-neutralizing component of the system and method of this invention as long as its pH is capable of neutralizing residual alkali on the hair.

The following discussion, therefore, is primarily directed to the hair brightener composition and hair relaxer system of this invention and to the hair brightening step of the method disclosed. The primary criteria for a useful hair brightening agent is that it be a cosmetically acceptable material which is substantially non-irritating and non-toxic to human skin at the amount used in practicing a hair brightener composition embodying the principles of this invention.

A hair brightener composition can contain sufficient acidifying agent or alkalizing agent to provide a physiologically acceptable pH of from about 2 to about 9, preferably from about 3 to less than about 7, more preferably from about 3.5 to about 4.5. The actual pH of the hair brightener composition is determined by the active brightening agent selected and the pH at which it is most effective cosmetically and most stable chemically.

The term "acidifying agent" denotes cosmetically useful mineral acids, such as phosphoric acid and hydrochloric acid, and organic acids containing about 2 to less than about 7 carbon atoms, zero to less than about 4 carboxyl groups and zero to less than about 4 hydroxyl groups per molecule and mixtures of each. Exemplary organic acids commonly used are acetic and citric. The term "alkalizing agent" refers to cosmetically useful inorganic and organic bases, such as sodium hydroxide, potassium hydroxide, sodium phosphate, ammonium hydroxide and organic primary-, secondary- or tertiary amines having about 2 to less than about 10 carbon atoms per molecule.

For purposes of screening hair brightening agents capable of enhancing or restoring a visibly natural tone to yellowed alkali-relaxed gray hair, materials were judged useful if they removed the yellow tone to at least a level intermediate to, and more preferably approximating, that of the corresponding unrelaxed hair and the unbrightened alkali-relaxed gray hair. The brightening efficacy was determined by visually ranking the treated hair using an arbitrary ranking scale of 1 to 5. A ranking of 1 represented the tone of the natural untreated virgin hair control and a ranking of 5 represented the yellowed tone of the alkali-treated hair. A material was judged useful if it produced a ranking of at least 3 and more preferably of 1 to 2 within a contact period of about 5 minutes in laboratory screening studies. This criteria was judged useful for predictively selecting materials as hair brightening agents capable of brightening yellowed alkali-relaxed gray hair in salon studies within a total contact time of less than about 15 minutes, preferably less than about 10 minutes, more preferably within about 0.5 minutes to about 5 minutes.

It was surprisingly found that active hair brightening agents comprising materials which are a source of relatively low concentrations of hydrogen peroxide equivalent in water successfully brightened dulled, yellowed gray relaxed hair. The term "relatively low hydrogen peroxide equivalent" denotes concentrations of hydrogen peroxide as free available $H_2O_2$ in water of about 0.2 weight percent to about 3 weight percent, preferably about 0.3 to about 2.5 weight percent, most preferably about 1 weight percent to about 2 weight percent.

Hair brightening was achieved with relatively low hydrogen peroxide equivalent over a physiologically acceptable pH range of from about 2 to about 9 without visibly bleaching the hair. Hair brightening materials which are sources or donors of hydrogen peroxide include per-compounds which release hydrogen peroxide in water and hydrogen peroxide. Hydrogen peroxide is particularly preferred.

Example per-compounds are substantially solid products of the addition of hydrogen peroxide with inorganic and organic compounds, inorganic peroxides, inorganic peracids, and inorganic peroxyhydrates which can be dissolved in water to release hydrogen peroxide equivalent for use. Exemplary cosmetically useful per-compounds include urea peroxide, sodium carbonate peroxide, sodium pyrophosphate peroxide, acidified sodium perborate tetrahydrate and polymeric complexes of hydrogen peroxide, such as polyvinylpyrrolidone and hydrogen peroxide.

It was also surprisingly and unexpectedly found that relatively high concentrations of cosmetically acceptable water-soluble aliphatic organic acid, having less than about 7 carbon atoms per molecule and one or more hydroxyl or mercapto substituent groups, and salts thereof preferably at a physiologically acceptable pH of less than about 5 also brightened yellowed alkali-relaxed hair. The term "relatively high" as applied to these acids denotes a concentration of above about 1 weight percent and less than about 6 weight percent, preferably about 5 weight percent. A hair brightening effect was most preferably achieved at a pH of about 3.5 to about 4.5 with hair brightener compositions containing certain organic acids and sufficient acidifying agent or alkalizing agent as described in more detail below.

Example water-soluble cosmetically useful aliphatic organic acids having one or more hydroxyl groups include adipic acid, citric acid, lactic acid, succinic acid, tartaric acid, malic acid and malonic acid. Citric acid is preferred. Example water-soluble cosmetically useful organic acids having mercapto groups include mercaptoacetic (thioglycolic) acid, 2-mercaptosuccinic (thiomalic) acid, 2,5- dimercaptoadipic acid, 2-amino-3-mercaptopropionic acid (cysteine), L-alpha-acetamido-beta-mercaptopropionic acid (N-acetyl-L-cysteine). Particularly preferred is 2-amino-3-mercaptopropionic acid and the hydrochloride salt thereof. The foregoing listings are provided by way of example and are not intended to be limiting.

The hair brightening efficacy of hydroxyl substituted organic acid was less than that of mercapto-substituted acid at a pH of about 3.5 to about 4.5 as illustrated in Examples 8 and 9 below, and both of the foregoing types of hair brightening agents were judged generally less effective and less preferred than hydrogen peroxide hair brightening agents for use within a short hair brightening contact time of about 5 minutes. Useful hair brightening compositions were prepared containing hydrogen peroxide as the primary active hair brightening agent in combination with hydroxyl substituted acid, such as citric acid, without losing efficacy. The mechanism by which each of the foregoing brightening agents brighten the yellowed hair is not fully understood.

Hydrogen peroxide in aqueous liquid form is particularly preferred as a brightening agent for convenience in handling and efficacy. Useful hydrogen peroxide is readily available commercially as a stabilized concentrated aqueous liquid from suppliers well-known in the cosmetic arts and can be diluted for use. For convenience, and not by way of limitation, hair brightener compositions are hereafter generally illustrated by referring to compositions prepared with liquid hydrogen peroxide as the active hair brightening agent, unless indicated otherwise.

It was further surprisingly found that other oxidizing agents which are known and used in the cosmetic arts, such as sodium bromate, alkaline sodium perborate tetrahydrate and sodium hypochlorite were substantially ineffective as hair-brightening agents as illustrated in Example 6 below. Additionally surprising was the finding that the organic acids, acetic, aminoacetic (glycine), ethylenediaminetetraacetic, and the N-substituted cysteine produced substantially little or no hair brightening even at relatively high concentrations of 5 weight percent in water during laboratory tests as illustrated in Examples 8 and 9 below.

In practicing hair brightening of relaxed hair by the principles of this invention with hydrogen peroxide, the amount of hydrogen peroxide equivalent present in a hair brightener composition is preferably at a concentration that is non-irritating to the skin and scalp, is used under pH conditions where alkaline-induced bleaching of hair is avoided or substantially minimal, and is in contact with yellowed relaxed hair only as long as necessary to visibly enhance and restore natural tones to yellowed hair.

So long as the strongly alkaline hair relaxer is removed from the hair and residual alkalinity on the hair is substantially removed and neutralized, preferably by treating the scalp and hair with a non-alkaline, base-neutralizing composition, the brightening efficacy of relatively low concentrations of hydrogen peroxide can be achieved without bleaching over a physiologically tolerable pH range of from about 2 to about 9. It is recognized that hair brightening also can be achieved at below or above these pH values, but are less preferred to avoid irritating the skin and scalp and are not necessary for achieving hair brightening.

Particularly surprising was that yellowed, relaxed hair was brightened substantially immediately on contacting the hair with a hair brightener composition containing about 1 weight percent to about 2 weight percent hydrogen peroxide at a pH of about 3 to less than about 6. In salon studies, by the time the hair brightener composition was applied to and distributed through the yellowed portion of the hair, the tone of the hair was visibly and desirably brightened to a natural tone. Yellowed fibers were "whitened" thereby restoring their natural silvery attractive bright highlights. The results were judged visually dramatic.

The contact time need to produce hair brightening under practical use conditions is determined by the volume of hair on the person's head, the length of time it takes to apply and distribute the hair brightener therethrough, the severity of the alteration to be corrected and the concentration of the hydrogen peroxide present. The hair brightener composition, therefore, need only be in contact with the hair for as long as needed to brighten the hair. Thus, brightening can be obtained in a total contact time of about 0.5 minutes to less than about 15 minutes, more frequently in less than about 10 minutes, most frequently in less than about 5 minutes. As the concentration of hydrogen peroxide decreases or increases, the length of contact time needed respectively increases or decreases.

Most of the strongly alkaline hair relaxers for professional or home use are sold in kits contain one or more hair conditioners packaged in separate containers for application to the hair either before during or after applying the hair relaxer. Likewise, a hair relaxer and post-relaxer hair brightener system encompassing the principles of this invention is preferably supplied in kit form and can include hair conditioning agents as separate packaged components for application before, during or after alkali-relaxing as discussed below. Preferably, effective hair conditioning amounts of hair conditioning agents are included in the hair brightener composition.

With reference to hair-conditioning, the term "effective hair-conditioning amount" means that a sufficient amount of hair conditioning agent, preferably a cationic compound, is present to either effect conditioning in some step of the relaxation process or to produce a detectable substantive conditioned effect on the relaxed hair upon drying when the relaxation process is completed, or in both steps.

The term "hair conditioning agent" as used herein refers to substantially water-soluble cationic compounds which under certain circumstances are substantive to hair. The term "conditioned effect" or "substantive conditioned effect" is used herein in its commonly understood meaning denoting desirable improvements in the characteristics of the hair over those same characteristics normally observed in the absence of the conditioning agent, such as easier combing of the wet or dry hair, increased luster, a silkier, smoother and softer tactile feel on the hair, more manageable setting and styling and the like. One or more of the foregoing desirable characteristics may be either apparent by a visual or tactile inspection of the relaxed hair or may be characteristics which can only be measured objectively.

Cationic compounds are preferred ingredients for inclusion in a conditioning hair brighter composition of this invention but are not limited thereto. Cationic compounds denote compounds having a net positive charge in water solution and are generally known and used in the cosmetic arts to improve the physical tactile characteristics of the hair. The choice of cationic compound is limited only by its solubility and its ability to effect conditioning during the relaxation process or to produce a substantive conditioned effect on the relaxed hair and does not interfere with or sacrifice the effectiveness of the hair relaxer or hair brightener.

Cationic compounds included any number of polymeric and non-polymeric materials are well known in the art. For example, cationic compounds include quaternary ammonium salts, quaternary cationic polymers and amine functional silicone polymers having a polar amine group which develops a net positive charge in an aqueous solution. Quaternary cationic polymers are preferred, and in particular, those which can also modify viscosity as thickeners. The term "quaternary cationic polymer" as used herein denotes polymers having at least one available quaternary nitrogen per molecule.

Particularly preferred are homopolymers and copolymers of quaternary diallyldialkylammonium salts, in which the alkyl group contains 1 to about 18 carbon atoms, and polymers thereof having an anionic portion derived from anionic monomers of acrylic acid and methacrylic acid. Particularly preferred are the chloride salts of these cationic homopolymers and copolymers in which the alkyl group is methyl or ethyl, which are available in a range of weight average molecular weights as aqueous compositions containing about 40 percent polymer solids sold under the trademark MERQUAT by The Calgon Corporation, subsidiary of Merck & Co., Pittsburgh, Pa.

For example, the homopolymer, dimethyldiallyl ammonium chloride (DMDAAC) has the CTFA name, Polyquaternium-6, is sold under the trademark MERQUAT-100 and is described as having a weight average molecular weight of approximately 100,000. A copolymer reaction product of DMDAAC with acrylamide monomers has the CTFA name, Polyquaternium-7, is described has having a weight average molecular weight of approximately 500,000 and is sold under the trademark MERQUAT-550. Another copolymer is the reaction product comprised of 80 percent by weight DMDAAC and 20 percent by weight of an anionic monomer of acrylic acid, has the CTFA name, Polyquaternium-22, is described as having a weight average molecular weight of about 1,300,000 and is sold under the trademark MERQUAT-280.

Polyquaternium-22 is particularly preferred. Details for the preparation of this material and its related polymers is described in U.S. Pat. No. 4,772,462 issued Boothe et al., the disclosures of which are incorporated herein by reference.

Other useful and preferred cationic polymers are cationic ether cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. It is recognized that a number of other cationic polymeric conditioning agents are commercially available and known that can also be used. The disclosure of the preferred cationic polymers, therefore, is not intended to limit the scope of this invention.

Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

Hair conditioning agents which are silicone-derived are also useful. Particularly preferred are dimethicones and amine-functional silicone polymers which develop a net positive charge on the polar amine group in water. Exemplary materials include dimethyl silicone fluids supplied under the trademarks Silicone Fluid 200 and Dow Corning 225 fluid in a range of viscosities and molecular weights, amodimethicone, and trimethylsilylamodimethicone, all supplied by Dow Corning, Midland, Mich.

Smaller molecule cationic non-polymeric compounds can also be utilized herein. Exemplary small-molecule conditioning agents can include monofunctional or difunctional quaternary ammonium compounds, such as stearyldimethylbenzylammonium chloride, dimethyl(hydrogenated tallow) ammonium chloride, and the like. Non-polymeric conditioning agents can also include a quaternary ammonium ethosulfate identified by the CTFA name Quaternium-75 and sold under the trademark FINQUAT by Finetex, Inc., Elmwood, N.J.; and the quaternary ammonium salts of gluconamide derivatives, such as gammagluconamidopropyldimethyl-2-hydroxyethylammonium chloride and minkamidopropyldimethyl-2-hydroxyethylammonium chloride identified respectively by the CTFA names Quaternium 22 and Quaternium 26. Details for the preparation of these latter two materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxypropylene-bis-1,3-dimethylstearyl ammonium chloride, designated the CTFA name, Hydroxypropyl Bis-stearyldimonium chloride. The preparation of these and other bis-quat materials is described in U.S. Pat. No. 4,734,277 and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. A number of structurally related materials of this type are sold under the trademarks CROQUAT and CROTEIN by Croda, Inc., New York, N.Y.

It should be understood that any of the foregoing hair conditioning agents can also be present in other conditioning products applied to alkali-relaxed hair as part of the grooming desired.

The viscosity of the hair brightener composition is preferably adjusted by including viscosity modifying thickening agents for convenience in applying the product to the hair without running or dripping. Thickening agents for cosmetics are well known and include nonionic surfactants, soaps, natural gum thickeners, chemically modified gums, synthetic polymeric viscosity modifying agents, such as carbomers, and quaternary cationic polymers capable of thickening, such as Polyquaternium-22 and Polyquaternium-10 discussed earlier.

A collected description of a number of polymers and thickeners used in cosmetics, their properties and suppliers can be found in the compilation edited by Lochhead, R., titled "Encyclopedia of Polymers and Thickeners for Cosmetics," published in *Cosmetics & Toiletries*, 103 (2) pp. 99–129 (1988) and elsewhere in that same publication. Other listings of polymers and thickeners, and their suppliers, can also be found in the *CTFA Cosmetic Ingredient Dictionary*, 3rd Ed., and its Supplement, published in 1982 and 1985, respectively, by the Cosmetic Toiletry and Fragrance Association, Inc. (hereafter CTFA Dictionary and CTFA name). The relevant disclosures of the foregoing are incorporated herein by reference.

The hair brightener composition can also include cosmetic adjuvants emulsifiers, surface-active agents, opacifying agents, product stabilizing agents, metal-ion chelating agents, preservatives, fragrance, product coloring agents and mixtures thereof, each present in effective amounts for their intended purposes. Useful hair brightener compositions are not restricted as to form or appearance. They can be prepared in the form of liquids, gels, lotions, paste, creams or in substantially solid anhydrous form as powders or tablets to be dissolved in water for use. The aqueous compositions can be substantially visibly clear, opaque or translucent, as desired. Substantially clear gels and water-in-oil emulsion compositions are preferred.

The chemical stability of hair brightener composition in which hydrogen peroxide is the active hair brightening agent is preferably retained over for long-term storage aging. Preferably, aqueous composition are prepared from liquid hydrogen peroxide stabilized by including sufficiently effective amounts of preservative and metal-ion chelating agents to retain an active hydrogen peroxide equivalent of at least above about 85 weight percent, preferably at least about 90 weight percent, more preferably about 95 weight percent on long-term storage ageing.

Techniques and analytical methods for determining the stability of liquid hydrogen peroxide are commonly known in the cosmetic arts and are available from the suppliers. One preferred method for predictively testing hydrogen peroxide stability is referred to herein as the "boil test".

Briefly described, the boil test comprises heating a 50 milliliter quantity of a composition containing hydrogen peroxide in a passivated flask placed in a water bath at about 66 degrees C. for seven days. The percent stability is determined from the change in the initial and final active hydrogen peroxide concentration and a stability value of about 90 percent or above generally can be expected to exhibit satisfactory shelf stability for at least about 12 months under normal room temperature storage conditions. Details of these and other analytical techniques are found in *FMC Technical Bulletin, No. 42*, available from FMC Corporation, Philadelphia, Pa., and the disclosures of which are incorporated herein by reference.

Particularly preferred is a pourable non-running oil-in-water emulsion in lotion form comprising hydrogen peroxide, at least one nonionic emulsifying agent, and a cationic hair conditioning agent, which is stable to phase separation on storage aging for at least six weeks at a temperature of about 45 degrees C. and has a boil test stability of at least about 85 weight percent hydrogen peroxide equivalent. Useful amounts of nonionic emulsifying agent and cationic hair conditioning agents can be as low as about 0.1 weight percent; the amounts being limited only by solubility, cost and efficacy and are readily determinable by formulation techniques known to those skilled in cosmetic emulsion arts.

Where active hydrogen peroxide hair brightening agent is obtained from substantially solid materials which form hydrogen peroxide when dissolved in water just prior to use, the chemical stability of the hydrogen peroxide need only be retained over the short term period of the alkali relaxing process.

When using a hair relaxer and hair brightener system of this invention in a no-base hair relaxer procedure, generally conventional alkali hair relaxing techniques are otherwise followed, except for the hair brightening step. The following discussion, therefore, describes several conditioning method aspects of practicing hair brightening. Simultaneous hair conditioning and hair brightening is achieved when hair conditioning agent is present in the hair brightener composition. Alternatively, hair brightening is achieved in the hair brightening step and hair conditioning is achieved in a separate step, as described.

In one hair conditioning method aspect, a hair conditioner composition is applied to the model's hair before the hair relaxer is applied without an intervening water rinse.

Otherwise, hair relaxer is commonly applied as follows. The model's hair is divided into four portions as delineated by the areas separated when hypothetical lines are drawn from ear-to-ear and from nose-to-backbone. Starting with the rear portions, a hair relaxer cream is applied to the virgin outgrowth or naturally curly portion of the hair with the back side of a comb (opposite from the teeth). This process takes about 8 minutes for treatment of all the model's hair.

Each portion of the hair is then physically smoothed with the comb back. The smoothing step helps to ensure adequate hair shaft penetration and softening by the relaxer and also puts tension on the hair to help in relaxing the curl in the hair. The smoothing step is then periodically repeated to facilitate relaxing or straightening until the desired amount of curl relaxation is achieved. The total time for smoothing (both the initial and repeat steps) normally takes from about 5 to about 10 minutes, depending upon the hair length and thickness. Thus, at this point, the relaxer is on the head for about 13 to about 18 or about 20 minutes.

The relaxer is then thoroughly and rapidly removed from the alkali-relaxed hair by rinsing with water having a temperature of about 37° C. (about 77° F.). The rinsing step is substantially immediately followed by washing with a non-alkaline, base-neutralizing shampoo. The shampoo is preferably buffered to a pH of less than about 7, preferably a pH of about 4 to about 6 so that residual alkali left in the hair or on the scalp is removed and neutralized. This shampooing step is usually repeated two or three times with intervening rinses.

In another conditioning method aspect, the alkali-relaxed hair may also be treated with a hair conditioner, before or after the shampooing step, to improve wet combing and hair feel, before brightening the hair. For example, in some cases, a hair conditioner having a pH of less than about 8 is applied before shampooing and the hair is then subsequentially shampooed with or without an intervening water rinse.

For practicing hair brightening the following procedure is used. Substantially immediately after the foregoing neutralizing and rinsing step, the substantially neutral alkali-relaxed hair is lightly blotted of excess water and visually observed for yellowing or undesirable tonal alteration. Hair brightener is then immediately applied to the hair and distributed through the hair to contact and brighten all visible altered fibers. As soon as the tone of the hair is visible enhanced and improved in natural appearance, the hair brightener is rinsed from the hair with water. Hair brightening is successfully achieved with no loss in hair relaxing effectiveness.

When a conditioning hair brightener of this invention is used, no extra post-brightening step is needed. The hair may then be set and dried in a desired coiffure as is known in the art. Alternatively, further finishing conditioners can be applied without losing the brightening effect achieved.

A hair relaxer system aspect for use in the above method preferably comprises at least three components: (i) a no-base hair relaxer cream, (ii) non-alkaline, base-neutralizing shampoo and (iii) a hair brightener encompassing the principles of this invention each contained in separate packages supplied in a kit. The active hair brightening agent can be packaged in a liquid form or supplied in a substantially solid form as a powder or tablets to be dissolved in water just before use. Where a no-lye hair relaxer cream is desired, the kit contains a two-part product of separately packaged liquid activator portion and alkaline cream portion as component (i).

A preferred conditioning hair relaxer system aspect comprises all of the foregoing components (i-iii), except that the hair-brightener component (iii) includes a hair-conditioning agent for simultaneously brightening and conditioning the alkali-relaxed hair during the hair brightening step. Another preferred conditioning hair relaxer system aspect comprises the foregoing components (i-iii) plus a hair-conditioning component (iv) intended to be applied to the hair in a separate step and is preferably supplied as a separately packaged component of a kit. Component (iv) can be applied in one or more of the conditioning steps discussed above and preferably has a pH of less than about 8, more preferably about 4 to about 6, and preferably contains a cationic compound. The cationic compound can include those described earlier and can be the same or different from cationic compounds present in the hair brightener composition.

The following Examples illustrates hair brightener compositions of this invention with generally preferred ingredients and methods of preparation, but are not intended to be limited thereby.

EXAMPLE 1

This example illustrates the efficacy of conditioning hair brightener compositions in simultaneously conditioning and brightening relaxed hair when a hair relaxer and hair brightener system of this invention is practiced. This example also illustrates the beneficial effective brightening of yellowed relaxed hair by Composition A containing about 1.6–1.8 percent hydrogen peroxide compared to a composition containing about 12 percent sodium bromate (Composition D) using a half-head comparative technique described below.

Hair brightener Compositions A, B and C were each prepared in the form of a substantially translucent pearlescent pourable lotion having the amounts shown below.

| No. | Ingredient | Weight Percent (as supplied) | | |
|---|---|---|---|---|
| | | A | B | C |
| 1 | Hydrogen peroxide (35%) (Note a) | 5 | 5 | 5 |
| 2 | Polyquaternium-10 (Note b) | 0.3 | 0.3 | 0.5 |
| 3 | Hydroxyethylcellulose (Note c) | 0.4 | — | 0.75 |
| 4 | Pearlescing agent (Note d) | 1 | 1 | 1 |
| 5 | Phosphoric acid to pH 3.5–4.5 (85%) | *Q.S. | Q.S | Q.S |
| 6 | Perfume (prestabilized) | Q.S | Q.S | Q.S |
| 7 | D&C Red #33 to pale tint | Q.S | Q.S | Q.S |
| 8 | Water to 100% final weight | Q.S | Q.S | Q.S |
| | Measured pH (initial) | 4.2 | 4 | 4.4 |
| | Weight % active $H_2O_2$ (analyzed) | 1.65 | 1.78 | N/A |

*Q.S. = a quantity sufficient.

a) Hydrogen peroxide Super D, supplied as a stabilized aqueous solution by FMC Corporation, Philadelphia, Pa.

b) POLYMER JR30M, a water-swellable cationic cellulosic resin supplied as a powder by Union Carbide Corporation, Danbury, Conn., which provides a Brookfield viscosity of about 1,000 to about 2,500 centipoises at 1 percent in water at 25° C. (Brookfield Model LVF, spindle No. 3 at 30 revolutions per minute (rpm) spindle speed).

c) A nonionic water-soluble cellulose ether polymer supplied by Amerchol Corporation, Edison, N.J. under the name CELLOSIZE POLYMER PCG-10, as a powder which provides a Brookfield viscosity of about 4,000 to about 6,000 centipoises (cps) at 1 percent in water at 25° C. (Brookfield Model LVF, spindle No. 4 at 30 rpm spindle speed) or by Aqualon Company under the name NATROSOL 250 in various viscosity grades.

d) INCROPEARL NI, Croda, Inc., New York, N.Y.

The compositions can be prepared by dissolving ingredient No. 2 in water (ingredient No. 6) at ambient room temperature with stirring and mixing until a substantially clear solution forms. Ingredient No. 3 is then added and dissolved in the clear solution with stirring and mixing until a substantially uniform and viscous mixture forms. The viscous mixture is then warmed to about 45° C. and about 50° C. and ingredient No. 4 is added with stirring to form a homogeneous mixture. The homogeneous mixture is then cooled with stirring to between about 25° C. and about 30° C., and ingredient No. 1 is then sequentially added with stirring. Ingredient No. 7 can be included in the same step with ingredient No. 4 or, alternatively, ingredient Nos. 4 and 7 can be premixed and added to the cooled mixture after the addition of ingredient Nos. 1 and 5. Ingredient No. 6 can be added to the cooled mixture before or after the addition of ingredient Nos. 1 and 5. The pH is then adjusted by adding ingredient No. 5.

A comparative salon study using a half-head technique described below (Protocol 1) was made of the hair brightening efficacy of Composition A over that of Composition D. Composition D was a commercial chemical oxidizing neutralizer for thiol-waved hair containing 12 percent sodium bromate. The remaining ingredients listed on the label of Composition B comprise nonionic surface-active agents, the thickener, hydroxyethylcellulose, as well as preservatives, product-stabilizing agents, fragrance and water.

A female volunteer whose hair characteristics were classifiable as "normal" with about 75 percent gray was given a treatment with a hair relaxer and post-relaxer hair brightener system by Protocol 1. The components of the hair relaxer system for this Protocol comprised: i) a commercial no-base, no-lye hair relaxer freshly prepared by mixing together the activator liquid and alkaline cream supplied in the kit by the manufacturer according to the manufacturer's instructions; ii) a non-alkaline, base-neutralizing shampoo commercially sold by the assignee of this invention under the trademark COLOR ALERT®; and iii) either Composition A as hair brightener or Composition B as brightener each being applied to opposing sides of the hair on the head.

The hair relaxer cream was left in contact with the hair for about 20 minutes and then removed by rinsing the hair thoroughly with tap water. The relaxed and rinsed hair was then immediately shampooed. The shampoo contained an acid-base indicator (phenolsulfonphthalein) to assist the user in determining when all of the residual alkalinity in the hair was substantially removed and the hair was substantially neutral. This was achieved by a change in the visible color of the shampoo lather from pink, indicating alkalinity, to white, indicating neutrality. Thus, several applications of the shampoo were applied, with intervening rinses. After the last application was rinsed out with water, when the hair was lightly blotted of excess water, the tone of the wet relaxed hair was observed and judged as visibly yellowed.

The left and right sides of the still damp head of yellowed hair were then defined by a center part from the forehead to the nape of the neck, and hair brightener applied as follows. Composition A was applied to the yellowed hair on the left side of the head and distributed through the hair from the scalp to the end tips. Composition B was similarly applied to the hair on the right side of the head. Each composition was then rinsed out with water within a period of less than 5 minutes contact per side.

Surprisingly, the tone of the yellowed hair on the left side was brightened and had its natural white highlight restored and enhanced substantially instantly on contact it with Composition A. On the contrary, the tone of the yellowed hair on the right side remained substantially unchanged by contact with Composition B.

Composition A again effectively brightened yellowed relaxed gray hair substantially instantly on contact or within 5 minutes in five additional salon studies using a whole head technique (Protocol 2). For this protocol, the hair relaxing and hair brightening system and procedure described above was followed, except that Composition A was applied to all of the head hair. The hair relaxers used for component (i) were various commercially available no-base, lye-type and no-base, no-lye hair relaxer creams including "mild," "regular" and "super" strength products, selected on the basis of each model's hair needs.

For these salon studies, five models each having gray hair classified individually as being about 25%, about 40%, about 50%, about 80% and about 100% gray were selected. In three of the salon studies, the hair relaxer component (i) was a no-base, no-lye type hair relaxer cream prepared fresh from activator and alkaline cream as described above and in the other two studies, the hair relaxer component (i) was a no-base, lye-type hair relaxer cream which was applied as supplied directly from its package.

In each instance, the neutral alkali-relaxed gray hair was visibly yellowed after the shampoo step and in the post-relaxing step Composition A again brightened the tone of that gray hair substantially instantly on contact or within less than about 5 minutes contact. The result was a visibly pleasing enhancement of the tonal brightness and restoration of a natural whiteness and highlight to the yellowed fibers. Additionally, in all instances, the brightened wet hair was judged easy to comb and conditioned, further illustrating that Composition A simultaneously brightened and conditioned alkali-relaxed hair regardless of the type of hair relaxer used.

Similar simultaneous brightening and conditioning results were obtained when Composition B was used as component (iii) in Protocol 2 in eleven additional salon studies. In six of these studies, the hair relaxer system employed as component (i) a no-base no-lye type hair relaxer cream with the remaining five systems employing a no-base lye-type hair relaxer. The following number of models (#) represented gray hair classified as: about 30% (1); about 40–45% (2); about 50% (3); about 75% (3); and about 95–100% (2).

EXAMPLE 2.

This example illustrates a hair brightener composition of this invention in the form of a liquid shampoo (Composition E). To 95 parts by weight of the commercially available non-alkaline base-neutralizing shampoo sold by the assignee of this invention under the trademark COLOR ALERT® described in Example 1 were added 5 parts by weight of 35 percent hydrogen peroxide. (See Note a, Ex. 1). According to the listing of ingredients on its label, the COLOR ALERT® shampoo contains amphoteric, anionic and nonionic surface-active agents, hydrolyzed animal protein, a quaternary cationic polymer (Polyquaternium-7), citric acid, product stabilizing preservatives, fragrance, the acid-base indicator, phenolsulfonphthalein, and water.

The shampoo brightener composition had a measurable pH of about 5.3 to about 5.4 and an average active hydrogen peroxide concentration of about 1.64 weight percent, based on triplicate analyses.

Composition E can be used in place of Composition A by following the hair relaxing and brightening system and method of Example 1, Protocol 2, to obtain similar brightening results.

This composition illustrates that successful hair brightening can be achieved without interference from the cosmetic adjuvants present in a shampoo formula.

EXAMPLE 3.

This example illustrates conditioning post-relaxer hair brighteners prepared in the form of a gel or lotion.

| No. | Ingredient | Weight Percent (as supplied) Composition | | | | |
|---|---|---|---|---|---|---|
| | | F | G | H | I | J |
| 1 | Hydrogen peroxide (35%) (Note a, Ex. 1) | 5 | 5 | 5 | 5 | 5 |
| 2 | Polyquaternium-22 (Note e) | 3 | — | 2 | — | 3 |
| 3 | Trimethylsilylamodimethicone (and) octoxynol-40 (and) isolaureth-6 (and) propylene glycol (Note f) | — | 6 | — | 6 | — |
| 4 | Propylene glycol | 2 | — | 5 | — | 2 |
| 5 | Hydroxyethylcellulose (Note c, Ex. 1) | 1 | — | 1 | 1 | 1.5 |
| 6 | Polyacrylamide (and) isoparaffin (and) laureth-7 (Note g) | — | 2.5 | — | — | — |
| 7 | Preservative | Q.S. | — | — | Q.S. | Q.S. |
| 8 | Metal-ion chelating agent | Q.S. | — | — | — | Q.S. |
| 9 | Phosphoric acid (85%) to pH 3.5–4.5 | — | Q.S. | Q.S. | Q.S. | Q.S. |
| 10 | Water to 100% final weight | Q.S. | Q.S. | Q.S. | Q.S. | Q.S. |
| | Measured pH | 4.2 | 4.5 | 3.9 | 4.1 | 4.7 |
| | Weight % active H₂O₂ (analyzed) | 1.87 | 1.7 | 1.8 | 1.85 | 1.77 |
| | Viscosity Brookfield LVT cps in thousands at 25° C.: | | | | | |
| | Spindle No. 3 at 6 rpm | — | 17 | 8.2 | 10 | — |
| | Spindle No. 3 at 12 rpm | 6 | — | — | — | — |
| | Spindle No. 4 at 12 rpm | — | 14 | 7.5 | — | — |
| | Spindle No. 4 at 30 rpm | — | — | — | — | 9.4 |
| | Boil Test Stability (%) | — | — | — | — | 92.7 | e) CTFA name for MERQUAT 280, an 80/20 w/w polymer of DMDAAC and acrylic acid, supplied by Calgon Corporation, Pittsburgh, Pa., having a viscosity (Brookfield LVF, spindle No. 4 at 60 rpm) of about 3,500–17,000 cps at an average molecular weight of approximately 1,300,000 as an aqueous solution with about 35–41 weight percent polymer solids.

f) CTFA name for Dow Corning Q2-7224 conditioning agent a non-crosslinking amine-functional silicone polymer supplied as an aqueous nonionic emulsion with about 35 weight percent silicone content, supplied by Dow corning Corporation, Midland, Mich.

g) CTFA name (tentative) for a thickening and stabilizing agent for emulsions supplied as an aqueous emulsion under the trademark SEPIGEL 305 by SEPPIC, France.

The compositions can be prepared by dissolving ingredient Nos. 2–8 in all or a portion of No. 10 or as recommended by each supplier and then sequentially adding ingredient Nos. 1 and 9 and any remaining portion of No. 10 to form a viscous mixture having the amounts shown. Compositions F, H and J form substantially clear gels and Compositions G and I form substantially opaque lotions.

The same volunteer female who had received the comparative hair relaxer and hair brightener system in Protocol 1 of Example 1 received, after an interval of about four months, a subsequent treatment with a hair relaxer and hair brightener system of this invention using Protocol 2 of Example 1, except that a commercial, no-base, lye-type relaxer was component (i) and Composition F as component (iii) of the system. Her gray hair was again visibly yellowed by the relaxer and brightened substantially immediately when Composition F was applied. Moreover, this model's hair was also simultaneously conditioned such that no further post-treatment conditioning product was needed.

Two additional salon studies were made on gray-haired models who received a hair relaxer and post-relaxer hair brightener system, following Protocol 2 of Example 1, with no-base no-lye relaxer, except that Composition F was used as component (iii). One model's hair was classified as being about 45% gray and the other's was classified as 100% gray (albino). In both instances, the tone of the model's gray hair was visibly yellowed by the alkali relaxer process and then brightened and naturalness enhanced and restored on contact with Composition F.

Similar rapid desirable brightening results on yellowed relaxed hair were also obtained either substantially immediately or within about 10 minutes maximum contact in 18 additional comparative salon studies. For these salon studies, Protocol 1 of Example 1 was followed, except that the hair relaxer type most suited for the model's hair was selected in each case and Compositions F and G were each applied on opposing sides randomly assigned.

In these studies, the hair of the individual models represented from about 10 percent to about 90 percent gray hair. The only criterion for qualifying the model for receiving a hair brightener treatment was that her hair be visibly yellowed by the alkaline relaxing process. In all 18 instances, both of the hair brightener compositions brightened dulled, yellowed, relaxed gray hair and restored to it a pleasing, bright appearance regardless of alkali-type relaxer used.

One model, having about 70–75% gray hair, had previously used a hair coloring shampoo which had left it undesirably colored. Both hair brightener compositions successfully removed even this discoloration. The results of these salon studies also illustrated that Compositions F and G were generally equivalent in hair brightening efficacy. The results also illustrated that both were capable of simultaneously conditioning and brightening the hair, differing only in degree of detectable or preferred conditioning result; Composition F being generally preferred over Composition G.

Similar brightening results and conditioning were obtained in twelve additional salon studies using various alkali relaxers following Protocol 2 of Example 1, except that Composition H was used in ten studies and Composition I was used in two studies as component (iii).

EXAMPLE 4.

This example illustrates compositions suitable as post-relaxer conditioning hair brighteners for practicing the disclosed hair relaxing and brightening method prepared in the form of relatively viscous yet pourable water-in-oil emulsions to contain about 1.75 weight percent to about 2 weight percent hydrogen peroxide at a pH of about 3.5 to about 4.5.

| No. | Ingredient | Weight Percent (as supplied) Composition | | | |
|---|---|---|---|---|---|
| | | K | L | M | N |
| | Phase A | | | | |
| 1 | Water to 100% final weight | Q.S. | Q.S | Q.S. | Q.S. |
| 2 | Metal ion-chelating agent | Q.S. | Q.S. | Q.S. | Q.S. |
| | Phase B | | | | |
| 3 | Cetyl alcohol | 4.5 | 2 | 3.5 | 2 |
| 4 | Glyceryl monostearate (and) PEG-100 stearate (Note h) | 2.5 | — | 2 | — |
| 5 | Laureth-23 (Note i) | 2 | — | 2 | — |
| 6 | Dimethicone (Note j) | 0.5 | — | 0.5 | — |
| 7 | Stearalkonium chloride (21% in propylene glycol) (Note k) | — | 6 | — | 6 |
| 8 | Oleth-20 (Note l) | — | 1 | — | 1 |
| 9 | Mineral Oil, light (Note m) | — | 2 | — | 2 |
| | Phase C | | | | |
| 10 | Hydrogen peroxide (35%) (Note a, Ex. 1) | 5 | 5 | 5 | 5 |
| | Phase D | | | | |
| 11 | Polyquaternium-22 (Note b, Ex. 1) | 3 | 3 | 3 | 3 |
| | Measured pH (initial) | 4 | 4.3 | 4 | 4.4 |
| | Weight % active $H_2O_2$ (analyzed) | N/A | 2 | N/A | 2.3 |
| | Viscosity Brookfield LVT cps in thousands at 25° C.: | | | | |
| | Spindle No. 3 at 6 rpm | 17 | — | — | — |

-continued

| No. | Ingredient | Weight Percent (as supplied) Composition | | | |
|---|---|---|---|---|---|
| | | K | L | M | N |
| | Spindle No. 3 at 12 rpm | — | — | 3.2 | 9.95 |
| | Spindle No. 4 at 12 rpm | — | 19.25 | — | 12.75 | h) CTFA name for blend of glycerol monostearate and polyethylene stearate, self-emulsifying, acid stable nonionic oil-in-water emulsifier commercially supplied under the trademarks LIPOMULSE 165 by Lipo Chemicals, Inc., Paterson, N.J. and ARLACEL 165 by ICI Americas, Inc., Wilmington, Del.

i) CTFA name for the 23 mole polyethylene glycol ether of lauryl alcohol, nonionic oil-in-water emulsifier commercially supplied under the trademarks LIPO-COL L-23 by Lipo Chemicals, Inc., Paterson, N.J. and BRIJ 35 by ICI Americas, Inc., Wilmington, Del.

j) CTFA name for dimethylsilicone fluids sold in a variety of viscosities and molecular weights by Dow Corning Corporation, Midland, Mich. under the trademark DOW CORNING 200 fluid, viscosity, 100 centistokes.

k) CTFA name for stearyldimethylbenzylammonium chloride supplied as an aqueous paste in propylene glycol under the designation DPSC325-32 by Sherex Chemical Company, Inc., Janesville, Wis., having a quaternary content of about 21 weight percent.

l) CTFA name for the 20 mole ethylene oxide adduct of oleyl alcohol nonionic oil-in-water emulsifier sold under the trademarks LIPOCOL L-20 by Lipo Chemicals, Inc., Paterson, N.J. and BRIJ 98 by ICI Americas, Inc., Wilmington, Del.

m) This mineral oil has a reported Saybolt viscosity at 100° F. of 50/60 S.U.S.; a viscosity of 7–10 centistokes at 40° C.; a specific gravity in the range of 0.822–0.833 at 25° C.

Phase A is prepared by dissolving ingredient No. 2 in No. 1 at a temperature of about 80° C. Phase B is prepared by combining ingredient Nos. 3–9 at a temperature of about 80° C. and then adding the heated combination to phase A with mixing agitation and mixing until homogenous. The homogenous mixture is cooled to between about 45° C. to about 55° C. to thicken. The thickened mixture is cooled to about 35° C. to about 40° C. and phases C and D are sequentially added while continuing cooling to ambient room temperature of about 25 C. The emulsions were judged effective as post-relaxer hair brighteners and conditioners.

EXAMPLE 5.

This example illustrates post-relaxer conditioning hair brightener compositions prepared in the form of relatively viscous yet pourable oil-in-water emulsions to contain about 1.75 weight percent to about 2 weight percent hydrogen peroxide at a pH of about 3.5 to about 4.5.

| No. | Ingredient | Weight Percent (as supplied) Composition | | | |
|---|---|---|---|---|---|
| | | N | O | P | Q |
| 1 | Water to 100% final weight | Q.S. | Q.S | Q.S. | Q.S. |
| 2 | Metal ion-chelating agent | Q.S. | Q.S. | Q.S. | Q.S. |
| 3 | Stearalkonium chloride (21% in propylene glycol) (Note k, Ex. 4) | 6 | — | 6 | 6 |

-continued

| No. | Ingredient | Weight Percent (as supplied) Composition | | | |
|---|---|---|---|---|---|
| | | N | O | P | Q |
| 4 | Carsoquat SDQ-25 (25% solids) (Note n) | — | 6 | — | — |
| 5 | Cetearyl alcohol (and) ceteareth-20 (Note o) | 2 | 2 | 2 | 2 |
| 6 | Cetyl alcohol | 1 | 1.5 | 1 | 1 |
| 7 | Mineral Oil, light (Note m, Ex. 4) | — | — | 0.5 | — |
| 8 | Preservative | Q.S. | Q.S. | Q.S. | Q.S. |
| 9 | Polyquaternium-22 (Note b, Ex. 1) | 3 | 3 | 3 | 3 |
| 10 | Hydrogen peroxide (35%) (Note a, Ex. 1) | 5 | 5 | 5 | 5 |
| 11 | Phosphoric acid (85%) to pH 3.5–4.5 | Q.S. | Q.S. | Q.S. | Q.S. |
| | Measured pH (initial) | 4.5 | 4.4 | 4.1 | N/A |
| | Weight % active $H_2O_2$ (analyzed) | 2 | 2 | N/A | N/A |
| | Viscosity Brookfield LVT cps in thousands at 25° C.: | | | | |
| | Spindle No. 4 at 30 rpm | 11.4 | 7.6 | 6.2 | 8.5 |
| | Boil Test Stability (%) | 92.3 | 92.7 | N/A | N/A | n) Water-soluble dispersion supplied under this name by Lonza, Inc., Fairlawn, N.J. reportedly containing about 21 weight percent stearyldimethylbenzyl ammonium chloride and related cationics, about 4 weight percent stearyl alcohol, about 5 weight percent isopropyl alcohol and about 70 weight percent water having the CTFA designation stearalkonium chloride.

o) CTFA name for a mixture of fatty alcohols consisting predominantly of cetyl and stearyl alcohols (cetearyl alcohol) and the 20 mole adduct of cetearyl alcohol (ceteareth-20) supplied under the name PROMULGEN D by Amerchol Corporation, Edison, N.J.

Composition N was prepared by heating and mixing together ingredient Nos. 1-3 and 5-6 at about 80 to 85 degrees C. until homogeneous, cooling the mixture to about 55 degrees or until it thickens, thereafter adding ingredient Nos. 8 and 9 and mixing with continued cooling and at about 45 degrees or less sequentially adding ingredient Nos. 10 and 11. Composition N has a storage stability of at least 6 weeks at a temperature of about 45 degrees C. without phase separation.

Composition O was prepared by heating and mixing together ingredient Nos. 1, 2 and 4-6 at about 70 degrees C. to about 75 degrees C. until homogeneous, then cooling the mixture to about 45 degrees or until it thickens, thereafter cooling and adding ingredient Nos. 8 and 9 at about 30 degrees to about 35 degrees C. and subsequently cooling to about 25 degrees C. and sequentially adding ingredient Nos. 10 and 11.

Compositions P and Q can be prepared by heating and mixing together ingredient Nos. 1-3 to 70 degrees C., preferably to about 80 degrees C. and about 85 degrees C., then adding ingredient Nos. 5-7 and mixing until homogenous, thereafter cooling the mixture to about 45 degrees C. and 50 degrees C. or until thickened, thereafter cooling further and incorporating ingredient Nos. 8-11 at a temperature of about 30 degrees C.

Thirteen salon studies were made on gray-haired models following Protocol 1 of Example 1, except that Composition N was applied on one side and Composition J of Example 3 was applied to the opposing side as component (iii). For these studies, 10 no-lye type and 3 lye type commercial hair relaxer creams were used and the individual models represented from about 10 percent gray hair to 85 percent gray hair. In all 13 instances, both of the hair brightener compositions brightened dulled, yellowed, relaxed gray hair and restored it to a pleasing, bright appearance.

The results of these salon studies illustrated that Compositions N and J were generally equivalent in hair brightening efficacy. The results also illustrated that both were capable of simultaneously conditioning and brightening the hair, differing only in degree of detectable or preferred conditioning result; Composition N being generally preferred over Composition J.

EXAMPLE 6.

This Example illustrates the hair brightening efficacy of weight percent concentrations of 0.35, 0.70 and 1.75 hydrogen peroxide at various pH's practiced in a hair relaxer and post-relaxer brightening method of this invention on gray hair. For this study, naturally gray caucasian hair was obtained from a commercial source (Ruth L. Weintraub Co., Inc., New York, N.Y.) and tresses of generally equivalent length and weight were prepared.

Each individual tress was treated with a commercial lye-type hair relaxer cream sold under the trademark BANTU by the assignee of this invention as follows. Sufficient hair relaxer cream was applied to cover and smoothed over the tress and left in contact with the hair for about 12 to about 15 minutes. The tress was then immediately rinsed thoroughly with tap water and shampooed with the non-alkaline, base-neutralizing shampoo described in Example 1, rinsed and towel blotted of excess wetness. The damp tress was then brightened by applying one of the following hair-brightening compositions and leaving it in contact for about 5 minutes, after which the tress was rinsed with tap water.

The tone of the hair brightening intensity was visually examined against that of untreated hair and ranked on a scale of 1 to 5, where 1=same as natural untreated virgin hair control; 2=substantially approaching natural brightness of untreated virgin hair control; 3=brightness intermediate that of untreated virgin hair and relaxed hair; 4=some marginal brightening noticeable; 5=no brightening, same as yellowed relaxed hair control. A ranking of 1-3 is considered effective hair brightening. The brightening intensity results follow:

| Percent $H_2O_2$* | Ranked Brightening Intensity At | | | |
|---|---|---|---|---|
| | pH 6 | pH 7 | pH 8 | pH 9 |
| 0.35 | 3 | 2 | 2 | 2 |
| 0.70 | 2 | 1 | 1 | 2 |
| 1.75 | 1 | 1 | 2 | 2 |

*The pH of each test solution was adjusted as needed with either phosphoric acid or ammonium hydroxide to pH 6, 7, 8 and 9.

The results illustrate that visual brightening of yellowed gray hair to a tone substantially approaching or equivalent to the natural tone of untreated unrelaxed hair was obtained within 5 minutes of post-relaxer contact time with either 0.70 weight percent or 1.75 weight percent hydrogen peroxide at all pH's, and with 0.35 weight percent hydrogen peroxide at pH's 7, 8 and 9.

At pH 6, intermediate brightening was obtained with 0.35 weight percent hydrogen peroxide and this level of efficacy was substantially unchanged by adjusting the pH to about 2 or to about 2.2 with about 5 weight percent and about 1 weight percent citric acid respectively, or to pH 2.6 with about 1 weight percent acetic acid. This result also illustrated that brightening was attributed more to the presence of an active concentration of hydrogen peroxide then to the pH of the medium. On further study, however, it was also found that, by slightly increasing the length of the post-relaxer contact time, the brightening efficacy of 0.35 weight percent hydrogen peroxide approached that of the higher peroxide concentration.

The results also showed that generally at above about pH 7, no additional visible brightening benefit was achieved at any of the foregoing active hydrogen peroxide concentrations.

EXAMPLE 7.

This example compares the hair brightening efficacy of aqueous hydrogen peroxide, urea peroxide, sodium perborate (alkaline and acidified) sodium hypochlorite practiced in a hair relaxer system and post-relaxing brightening method of this invention.

A commercial, two-part, no-base, no-lye hair relaxer kit was used, and the hair relaxer cream was prepared for use by mixing the activator part and alkaline cream part according to the manufacturer's instructions. The tresses were prepared and the hair relaxed generally following the same procedure of Example 6, except that the hair relaxer remained in contact with the hair for about 15 to about 18 minutes and after the base-neutralizing step, one of the following aqueous solutions was applied in the post-relaxer brightening step. The brightening intensity (BI) results which were ranked, as described in Example 6, follow:

| Post-Relaxer Rinse* | pH | BI |
|---|---|---|
| 1% Urea peroxide (0.35% as H$_2$O$_2$) | 4.2 | 3 |
| 5% Urea peroxide (1.75% as H$_2$O$_2$) | 4.0 | 2 |
| 0.35% Hydrogen peroxide | 3.4 | 2 |
| 1.75% Hydrogen peroxide | 3.7 | 1 |
| 0.35% Sodium perborate tetrahydrate | 9.3 | 5 |
| 1% Sodium perborate tetrahydrate | 3.7 | 3 |
| 1.75% Sodium perborate tetrahydrate | 9.9 | 4 |
| 5% Sodium perborate tetrahydrate | 3.8 | 2 |
| 0.35% Sodium hypochlorite | 8.3 | 5 |
| 1.75% Sodium hypochlorite | 8.5 | 5 |
| Control, virgin hair | — | 1 |
| Control, alkali-relaxed hair (yellowed) | — | 5 |

*All rinse compositions were freshly prepared on a weight percent basis as water solutions and the pH was adjusted where necessary with dropwise addition of aqueous 10 weight percent phosphoric acid.

The results show that within 5 minutes contact, the hydrogen peroxide, urea peroxide and acidified sodium perborate rinses effectively brightened, enhanced and restored the natural tone of the yellowed alkali-relaxed gray hair. Contrarily, rinses of sodium hypochlorite and alkaline sodium perborate were judged substantially ineffective within that short contact time.

EXAMPLE 8.

This example illustrates and compares the hair brightening efficacy of post-relaxer rinses of aliphatic organic acids, having hydroxyl or mercapto substituent groups, practiced in a hair relaxer system and post-relaxing brightening method of this invention at a physiologically desirable pH of about 3.5 to about 4.5.

The procedure of Example 7 was followed for preparing the tresses, preparing the no-base, no-lye hair relaxer cream and for relaxing the hair, except that one of the following aqueous solutions was applied in the post-relaxer brightening step. The brightening intensity (BI) results, ranked as described in Example 6, follow.

| Post-Relaxer Rinse* | pH | BI |
|---|---|---|
| 1% Citric acid | 3.5 | 4 |
| 5% Citric acid | 3.2 | 3 |
| 1% Aminoacetic acid | 3.8 | 5 |
| 5% Aminoacetic acid | 3.8 | 4 |
| 1% Mercaptoacetic acid | 3.5 | 3 |
| 5% Mercaptoacetic acid | 3.5 | 2 |
| 1% 2-Mercaptosuccinic acid | 3.9 | 3 |
| 5% 2-Mercaptosuccinic acid | 3.6 | 2 |
| 1% 2,5-Dimercaptoadipic acid | 3.5 | 3 |
| 1% 2-Amino-3-mercaptopropionic acid hydrochloride | 4.2 | 3 |
| 5% 2-Amino-3-mercaptopropionic acid hydrochloride | 3.8 | 2 |
| 1% L-alpha-acetamido-beta-mercaptopropionic acid | 3.6 | 5 |
| 5% L-alpha-acetamido-beta mercaptopropionic acid | 3.2 | 5 |
| Control, virgin hair | — | 1 |
| Control, alkali-relaxed hair (yellowed) | — | 5 |

*All rinse compositions were freshly prepared on a weight percent basis as water solutions and the pH was adjusted where necessary with dropwise addition of aqueous 10 weight percent phosphoric acid.

The results show that at pH 3.5–4.5, some intermediate brightening can be achieved within 5 minutes contact time with either a relatively high concentration (5%) of citric acid or at a concentration of 1% of the mercapto-organic acids. The brightening efficacy of the mercapto-organic acid increased as its concentration increased to 5% reaching a level of brightening judged substantially approaching that obtained with 0.35 weight percent hydrogen peroxide in Example 7. On the other hand, the non-mercapto acid, aminoacetic acid, and N-substituted mercapto acid were judged substantially weak to ineffective as hair brightening agents within a 5-minute contact time.

EXAMPLE 9.

This example illustrates and compares the hair brightening efficacy of organic acids against hydrogen peroxide as post-relaxer rinses practiced in a hair relaxer system and post-relaxing brightening method of this invention at a pH of from about 2 to about 4.5.

The procedures of Example 6 for preparing tresses, relaxing the hair with no-base, lye-type hair relaxer and ranking the brightening intensity (BI) of the hair was followed, except that the following post-relaxer rinses were used.

| Post Relaxer Rinse* | pH | BI |
|---|---|---|
| 1% Citric acid | 2.4 | 4 |
| 5% Citric acid | 2 | 3 |
| 1% Acetic acid | 3.1 | 4 |
| 5% Acetic acid | 2.7 | 4 |
| 1% Ethylenediaminetetracetic acid | 2.4 | 5 |
| 5% Ethylenediaminetetracetic acid | 2.4 | 5 |
| For comparison | | |
| 1.75% Hydrogen peroxide | 4.5 | 1 |

*Weight percent in water

The results show that intermediate brightening was again achieved within 5 minutes contact with a relatively high (5%) concentration of citric acid. On the other hand, acetic acid and ethylenediaminetetraacetic acid were each judged substantially weak to ineffective as hair brightening agents with such short contact time.

In further similar tests, a post-relaxer rinse of either 1 percent or 5 percent by weight phosphoric acid at pH 1.6–1.9 was also judged substantially ineffective as a hair brightening agent (B.I. rank of 5) in a 5-minute contact time.

The present invention has been described generally and with respect to preferred embodiments. It will be understood that modifications and variations of the disclosed method and compositions may be made without departing from the spirit and scope of the novel concept of the present invention.

We claim:

1. A method for the alkali-type relaxing of naturally curly hair and the post-relaxing brightening of said resulting alkali-relaxed hair whose tone is in need of brightening, the method comprising the steps of sequentially:
   a) applying to said curly hair a highly-alkaline hair relaxer composition having a pH above about 12 and containing an effective hair-relaxing amount of strong base;
   b) smoothing said applied composition physically through said hair periodically to facilitate relaxing and leaving said so-applied composition in contact with said hair until at least some of the natural curl in said hair is relaxed wherein said contact further visibly alters the tone of said hair, thereby to provide alkali-relaxed hair;
   c) removing substantially all of said so-applied composition from said alkali-relaxed hair by rinsing said hair at least once with water;
   d) applying to and distributing through said so-rinsed hair an effective amount of a non-alkaline, base-neutralizing composition to substantially neutralize and complete the removal of substantially all residual alkalinity therefrom in at least one application, and terminally rinsing the resulting hair at least once with water, thereby to provide substantially neutral alkali-relaxed hair whose tone is in need of brightening;
   e) contacting said neutral alkali-relaxed hair with an aqueous post-relaxer, hair brightener composition comprising water having dissolved therein an effective amount of at least one active hair brightening agent and having a physiologically acceptable pH, and leaving said hair brightener in said hair contact for a time period at least sufficient to visibly brighten the tone of said neutral alkali-relaxed hair; and
   f) removing said hair brightener composition from the so-brightened hair by rinsing said hair with water, thereby to provide alkali-relaxed and brightened hair,
   whereby the tone of said alkali-relaxed and brightened hair is substantially enhanced or restored.

2. The method of claim 1, wherein the strong base in step (a) comprises a member of the group consisting of water-soluble alkali metal hydroxides, alkali earth metal hydroxides, alkali earth metal oxides and relatively strong organic bases.

3. The method of claim 1, wherein the hair brightening agent comprises a material which is a source of hydrogen peroxide, present in an amount sufficient to provide about 0.2 weight percent to about 3 weight percent hydrogen peroxide equivalent and said contact is for about 0.5 minutes to less than about 15 minutes.

4. The method of claim 3 wherein the hair brightening agent is a member of the group consisting of hydrogen peroxide and water-soluble per-compounds which release hydrogen peroxide in water and said pH is about 2 to about 9.

5. The method of claim 1 wherein the hair brightener composition has a pH of about 3 to less than about 7 and the brightening agent is hydrogen peroxide present at an active concentration of about 1 weight percent to about 2 weight percent, and said contact is for about 0.5 minutes to less than about 10 minutes.

6. The method of claim 1, wherein the hair brightener composition has a pH of about 3 to less than about 7 and the hair brightening agent is urea peroxide present at a concentration of about 0.5 weight percent to about 5 weight percent, and said contact is for about 0.5 minutes to less than about 15 minutes.

7. The method of claim 1, wherein the hair brightening agent is a water-soluble aliphatic organic acid having less than about 7 carbon atoms per molecule and one or more hydroxyl or mercapto substituent groups or is a salt thereof and is present at a concentration of about 1 weight percent and less than about 6 weight percent and said pH is less than about 5.

8. The method of claim 1, wherein the hair brightener composition further includes cosmetic adjuvants selected from the group consisting of hair-conditioning agents, emulsifying agents, surface-active agents, opacifying agents, product stabilizing agents, viscosity modifying agents, metal-ion chelating agents, preservatives, fragrance, product coloring agents, and mixtures thereof.

9. The method of claim 1, wherein the hair brightener composition further contains an effective amount of a hair-conditioning agent and simultaneously brightens and conditions the hair in step (e).

10. The method of claim 9, wherein the conditioning agent is a cationic compound selected from the group consisting of quaternary ammonium salts, quaternary cationic polymers, amine functional silicone polymers having a polar amine group which develops a net positive charge in aqueous solution, and mixtures thereof.

11. The method of claim 10, wherein the cationic compound is a polymer selected from the group consisting of homopolymers and copolymers of quaternary diallyldialkyl ammonium salts in which each alkyl group per molecule contains 1 to about 18 carbon atoms, polymers thereof having an anionic portion derived from the group consisting of acrylic acid and methacrylic acid, and salts thereof.

12. The method of claim 11, wherein the cationic polymer is Polyquaternium-22.

13. The method of claim 10 wherein the cationic compound is a cationic ether cellulose.

14. The method of claim 13 wherein the cationic compound is Polyquaternium-10.

15. The method of claim 1, further including a hair-conditioning step performed in at least one of the following locations in the process step sequence:
   (i) before step (a);
   (ii) between steps (c) and (d); and
   (iii) a combination of each of step (i) and step (ii);
   said hair-conditioning step comprising applying to said hair a composition having a pH of less than about 8 and comprising an effective hair-conditioning amount of a cationic compound, said application optionally being followed by at least one water rinse.

16. The method of claim 15, wherein the cationic compound is selected from the group consisting of quaternary ammonium salts, quaternary cationic polymers, amine functional silicone polymers having a polar amine group which develops a positive charge in water and mixtures thereof.

17. The method of claim 15 wherein the hair relaxer is in the compositional form of a no-base hair relaxer cream, the base-neutralizing composition is in the compositional form of a shampoo having a pH of less than about 7, and the post-relaxer hair brightener composition is in the compositional form of a liquid comprising about 1 weight percent to about 2 weight percent hydrogen peroxide in water and having a pH of from about 3 to less than about 7.

18. The method of claim 1, wherein the hair relaxer comprises a strong base selected from the group consisting of sodium hydroxide, lithium hydroxide, and guanidine hydroxide; the base-neutralizing composition has a pH of less than about 8; and the post-relaxer hair brightener composition comprises about 1 weight percent to about 2 weight percent hydrogen peroxide and sufficient acidifying agent to provide a pH of about 3 to less than about 7 and the contact time in step (e) is for about 0.5 minutes to less than about 10 minutes.

19. An article of manufacture for relaxing naturally curly hair under highly alkaline conditions and post-relaxing brightening of the tone of said resulting relaxed hair comprising a hair relaxer and post-relaxer hair brightener system comprising at least three separate compositions, each composition being usable in a single one of a programme series of steps that are sequentially followed in a single hair relaxing procedure with at least one intervening rinsing with water to substantially remove each of said previously so-applied composition, wherein each composition individually comprises:
   i) a first highly-alkaline hair relaxer cream having a pH of above about 12 and containing an effective hair-relaxing amount of strong base;
   ii) a second aqueous, non-alkaline, base-neutralizing shampoo composition having a pH of less than about 8; and
   iii) a third aqueous post-relaxer hair brightener composition comprising water, having dissolved therein an effective amount of an active hair brightening agent and having a physiologically acceptable pH
   said compositions each being hair applicable and being usable in the numerical sequence stated.

20. The system of claim 19, wherein the aqueous hair brightening agent comprises a material which is a source of hydrogen peroxide, present in an amount sufficient to provide about 0.2 weight percent to about 3 weight percent hydrogen peroxide equivalent, and said pH is about 2 to about 9.

21. The system of claim 20, wherein the hair brightening agent is a member of the group consisting of hydrogen peroxide and water-soluble per-compounds which release hydrogen peroxide in water.

22. The system of claim 19, wherein the hair brightening agent is hydrogen peroxide at a concentration of about 1 weight percent to about 2 weight percent, and said pH is about 3 to less than about 7.

23. The manufacture of claim 19, wherein said system further includes a separate fourth hair conditioning composition, said hair conditioning composition comprising an effective hair conditioning amount of a cationic compound,
   said fourth composition being hair applicable and being usable in the numerical sequence stated sequentially following the application of said third composition.

24. A hair relaxer and post-relaxing hair brightener kit containing each one of said compositions of the system of claim 23 supplied in separate packaged form.

25. The kit of claim 24 including a hair brightener composition containing a hair brightening agent comprising a material which is a source of hydrogen peroxide, present in an amount sufficient to provide about 0.2 weight percent to about 3 weight percent hydrogen peroxide equivalent.

26. The system of claim 19, wherein the hair brightening agent is a water-soluble aliphatic organic acid having less than about 7 carbon atoms per molecule and one or more hydroxyl or mercapto substituent groups or is a salt thereof and is present at a concentration of about 1 weight percent and less than about 6 weight percent and said pH is less than about 5.

27. A kit containing a plurality of packages each one comprising a composition to be employed in a process for alkali-type relaxing and post relaxing brightening of said resulting alkali-relaxed hair, said kit comprising at least three separate compositions supplied in 28. The kit of claim 27, wherein the hair brightening agent comprises a material which is source of about 0.2 weight percent to about 3 weight percent hydrogen peroxide equivalent in water solution.

29. The kit of claim 28, wherein the hair brightening agent is a member of the group consisting of hydrogen peroxide and water-soluble per-compounds which release hydrogen peroxide in water and said pH is about 2 to about 9.

30. The kit of 29, wherein the hair brightening agent is hydrogen peroxide.

31. The kit of claim 27, wherein the hair brightener composition has a pH of about 3 to less than about 7 and the hair brightening agent comprises about 1 weight percent to about 2 weight percent hydrogen peroxide.

32. The kit of claim 27, wherein the hair brightener composition is packaged for use in a compositional aqueous form selected from group consisting of a gel, cream, paste, lotion, and liquid and in a substantially solid form selected from the group consisting of substantially anhydrous powders and tablets to be dissolved in water.

33. The kit of claim 27, wherein the hair brightener composition further includes cosmetic adjuvants selected from the group consisting of hair-conditioning agents, emulsifying agents, surface-active agents, opacifying agents, product stabilizing agents, viscosity modifying agents, metal-ion chelating agents, preservatives, fragrance, product coloring agents, and mixtures thereof.

34. A composition for brightening the tone of substantially neutral alkali-relaxed hair, the composition comprising water having an effective hair brightening amount of active hair brightening agent dissolved therein, wherein the hair brightening agent is selected from the group consisting of water-soluble aliphatic organic acids having less than about 7 carbon atoms per molecule and one or more hydroxyl or mercapto substituent groups and salts thereof present at a concentration of about 1 weight percent and less than about 6 weight percent and having a pH of less than about pH 6.

35. The post-relaxer hair brightener composition of claim 34 included in a hair relaxer kit containing a composition for relaxing hair at a pH above about 12.

36. In a method for relaxing naturally curly gray hair, in which the hair is relaxed at a pH above about 12 with an aqueous hair relaxer composition containing a strong base, wherein the hair so-relaxed is subsequently rinsed free of excess strong base with water and thereafter is substantially neutralized of residual alkalinity with a non-alkaline, base-neutralizing composition and the hair so-neutralized is then rinsed with water and wherein the natural tone of the relaxed hair is altered by said relaxing method, the improvement comprising the steps of brightening said relaxed hair to enhance and restore a natural tone to the relaxed hair by (i) applying a post-relaxer hair brightener composition to the substantially neutral, relaxed hair, wile it is still substantially wet from said water rinsing, said hair brightener composition comprising water, an effective amount of an active hair brightening agent and a sufficient amount of pH adjusting material selected from the group consisting of acidifying agents and alkalizing agents to provide a physiologically acceptable pH of about 2 to about 9, (ii) leaving said composition in contact with the hair for about 0.5 minutes to less than about 15 minutes and (iii) thereafter rinsing the so-brightened hair with water.

37. The method of claim 36, wherein the hair brightening agent comprises a material which is a source of hydrogen peroxide, present in an amount sufficient to provide about 0.2 weight percent to about 3 weight percent hydrogen peroxide equivalent in said hair brightener composition.

38. The method of claim 36, wherein the hair brightening agent is a member of the group consisting of hydrogen peroxide and water-soluble per-compounds which release hydrogen peroxide in water.

39. The method of claim 36, wherein the composition has a pH of about 3 to less than about 7 and the hair brightening agent is hydrogen peroxide present at an active concentration of about 1 weight percent to about 2 weight percent and the contact time is about 0.5 minutes to less than about 10 minutes.

40. An oil-in-water emulsion for the post-relaxer brightening and restoring of the tone of substantially neutral alkali-relaxed hair, the oil-in-water emulsion comprising an active hair brightening agent which is a source of about 0.2 to about 3 weight percent hydrogen peroxide equivalent; at least one nonionic emulsifying agent; and effective hair-conditioning amount of Polyquaternium-22, a sufficient amount of acidifying agent to provide a pH of about 3 to less than about 7 and water.

41. The composition of claim 40, wherein the hair brightening agent provides about 0.2 to about 3 weight percent hydrogen peroxide equivalent, said composition being stable to phase separation on storage at about 45 degrees C. for at least about six weeks and retaining an active hydrogen peroxide stability of at least above about 85 weight percent.

42. A kit containing one or more compositions for relaxing and post-relaxing brightening of hair including the composition of claim 40.

* * * * *

UNITED STATES PATENT AND TRADEMARK OFFICE
CERTIFICATE OF CORRECTION

PATENT NO. : 5,293,885

DATED : March 15, 1994

INVENTOR(S) : Adu G. Darkwa & Apolonio Villanueva, III

It is certified that error appears in the above-identified patent and that said Letters Patent is hereby corrected as shown below:

Column 30, claim 27, lines 19-23 should read:

27. A kit containing a plurality of packages each one comprising a composition to be employed in a process for alkali-type relaxing and post relaxing brightening of said resulting alkali-relaxed hair, said kit comprising at least three separate compositions supplied in separate packages, wherein each composition individually comprises:

a) an alkali-type hair relaxer composition, said composition having at the time it is in contact with said hair a pH above about 12 and including an effective hair relaxing amount of a strong base capable of relaxing at least some of the curl in naturally curly hair when said composition is in said contact;

b) a non-alkaline, base-neutralizing composition which is capable of neutralizing substantially all residual alkalinity remaining on said hair which has been previously relaxed with the hair relaxer composition of package (a) after said hair relaxer composition has been removed from the relaxed hair and said base-neutralizing composition is in contact with said relaxed hair; and c) a post-relaxer hair brightener composition comprising an effective amount of an active water-soluble hair brightening agent, said composition being at the time it is in contact with said hair the compositional form of an aqueous solution having a physiologically acceptable pH, and said hair brightening agent being capable of brightening the tone of said previously so-relaxed and neutralized hair when the tone of said hair is in need of brightening and said hair brightener composition is in contact with said hair for less than about 15 minutes.

UNITED STATES PATENT AND TRADEMARK OFFICE
CERTIFICATE OF CORRECTION

PATENT NO. : 5,293,885
DATED : March 15, 1994
INVENTOR(S) : Adu G. Darkwa & Apolonio Villanueva, III It is certified that error appears in the above-indentified patent and that said Letters Patent is hereby corrected as shown below:

Column 32, claim 40, line 17, change "and" to --an--.

Signed and Sealed this

Thirteenth Day of September, 1994

Attest:

BRUCE LEHMAN

Attesting Officer          Commissioner of Patents and Trademarks